(12) United States Patent
Omura et al.

(10) Patent No.: US 9,000,194 B2
(45) Date of Patent: Apr. 7, 2015

(54) MANGROMICIN COMPOUND AND PRODUCTION METHOD THEREFOR

(75) Inventors: Satoshi Omura, Tokyo (JP); Yoko Takahashi, Tokyo (JP); Takuji Nakashima, Tokyo (JP); Kazuhiko Otoguro, Tokyo (JP); Kazuro Shiomi, Tokyo (JP); Masato Iwatsuki, Tokyo (JP); Atsuko Matsumoto, Tokyo (JP)

(73) Assignee: The Kitasato Institute, Tokyo (JP)

( * ) Notice: Subject to any disclaimer, the term of this patent is extended or adjusted under 35 U.S.C. 154(b) by 0 days.

(21) Appl. No.: 14/342,311

(22) PCT Filed: Aug. 31, 2012

(86) PCT No.: PCT/JP2012/005541
§ 371 (c)(1),
(2), (4) Date: Feb. 28, 2014

(87) PCT Pub. No.: WO2013/031239
PCT Pub. Date: Mar. 7, 2013

(65) Prior Publication Data
US 2014/0206889 A1    Jul. 24, 2014

(30) Foreign Application Priority Data
Sep. 2, 2011 (JP) .................. 2011-191404

(51) Int. Cl.
C07D 321/00 (2006.01)
C07D 493/16 (2006.01)
C07D 493/18 (2006.01)
C12P 17/18 (2006.01)
C12R 1/01 (2006.01)

(52) U.S. Cl.
CPC ............ *C07D 493/16* (2013.01); *C07D 493/18* (2013.01); *C12P 17/181* (2013.01); *C12R 1/01* (2013.01)

(58) Field of Classification Search
USPC ........................................... 549/267
See application file for complete search history.

(56) References Cited

FOREIGN PATENT DOCUMENTS

WO    WO 2009/004899 A1    1/2009

OTHER PUBLICATIONS

Nakashima et al. The Journal of Antibiotics (2014) 67, 253-260.*
Hashida et al., 2010, abstracts of 130th Annual Meeting of Pharmaceutical Society of Japan 2, p. 102, 29TG-am03, with English translation.
Ishiyama et al., "In Vitro and in Vivo Antirypanosomal Activity of Two Microbial Metabolites, KS-505a and Alazopeptin", J. Antibiot., vol. 61, No. 10 (2008) pp. 627-632.
Nizuma et al., 2010, abstracts of 130th Annual Meeting of Pharmaceutical Society of Japan 2, p. 102, 29TG-am02, with English translation.
Igarashi, Y. et al., "Akaeolide, a Carbocyclic Polyketide from Marine-Derived Streptomyces", Organic Letters, vol. 15, No. 22, pp. 5678-5681, 2013.
Nakashima, T. et al., "Mangromicins, six new anti-oxidative agents isolated from a culture broth of the actinomycete, Lechevalieria aerocolonigenes K10-0216", J. of Antibiotics, pp. 1-7, 2014.

* cited by examiner

*Primary Examiner* — Nizal Chandrakumar
(74) *Attorney, Agent, or Firm* — Birch, Stewart, Kolasch & Birch, LLP

(57) ABSTRACT

The present invention addresses the problem of providing an anti-trypanosomal drug having a novel skeleton, in order to solve issues that occur with conventional technologies.
The present invention is based on the discovery of a microbe that produces an anti-trypanosomal drug having a novel skeleton. Specifically, this invention provides: a compound indicated by formula (I) having a trypanosomal inhibitory activity; an analog thereof; a production method therefor; and a *Lechevalieria* sp. K10-0216 strain that produces said compound.

5 Claims, No Drawings

MANGROMICIN COMPOUND AND PRODUCTION METHOD THEREFOR

TECHNICAL FIELD

The present invention belongs to the field of inhibition of proliferation of *trypanosoma* protozoa. Specifically, the present invention relates to compounds having activity to inhibit proliferation of *trypanosoma* protozoa, which are effective as veterinary medicines and pharmaceutical products, as well as production methods and use of said compounds.

BACKGROUND ART

Trypanosomiasis includes African sleeping sickness which is prevalent in Africa, and Chagas disease which is prevalent in South America. Trypanosomiasis that is called as African sleeping sickness or as human African trypanosomiasis is a reemerging protozoan infectious disease and number of people infected is estimated to be 18.3 million or more in a year and number of people died from said disease is considered to be about 50,000 in a year. Particularly, *trypanosoma* protozoa that are parasitic in humans are classified into two types, i.e., *Trypanosoma brucei gambiense* and *T. b. rhodesiens*, the former causes chronic sleeping sickness and the latter causes acute sleeping sickness. Trypanosomiasis is infectious disease with high mortality. In the last stage of infection, *trypanosoma* protozoa migrate into the central nervous system, and 80% or more of infected patients fall into a coma and eventually die. These *trypanosoma* protozoa are transmitted by tsetse fly which inhabits only Africa.

*Trypanosoma brucei gambiense* (*T. b. gambiense*) and *Trypanosoma brucei rhodesiens* (*T. b. rhodesiens*) are zoonotic parasitic species, which can parasitize farm animals such as cows, horses and sheep as well as wild animals such as gazelles and gnus. These animals serve as reservoir hosts, while they themselves do not develop trypanosomiasis. Further, another *trypanosoma* protozoa parasitize farm animals but not humans, that include, for example, *T. brucei brucei* (nagana) which belongs to the subgenus *Trypanosoma* and *T. vivax vivax* (souma) which belongs to the subgenus *Duttonella*, and animals infected with these protozoa follow a lethal course of infection depending on the animal species. These protozoa are also transmitted by tsetse fly.

Tsetse flies live in a region over 1,000 square km extended from the East coast to the West coast of the sub-Saharan African continent across 36 countries. Currently 150 million or more farm animals are exposed to the threat of said trypanosomiases. Moreover, there are non-tsetse fly-mediated *trypanosoma* protozoa that infect animals via, for example, mechanical transmission by blood-sucking insects such as horse fly and stable fly, which include *T. evansi* (surra) and *T. equiperdum* (dourine), both of which are subgenus *Trypanosoma*. Particularly, surra has developed into a pandemic spreading over Africa, Latin America, Southeast Asia, China, Middle East, India, and other regions. Recently, surra tends to become epidemic spread, making surra the most alarming animal trypanosomiasis in invasion of Japan.

Existing anti human-infectious *trypanosoma* agents against these *trypanosoma* protozoa, including classic drugs such as suramin (developed in 1923), pentamidine (developed in 1939) and melarsoprol (developed in 1953) as well as chemically-synthesized pharmaceutical products such as eflornithine (developed in 1978) have been used for long time, during the last half-century. Although suramin is effective in the initial stage of infection with *T. b. gambiense* and *T. b. rhodesiens*, it is nephrotoxic.

Pentamidine is effective in the initial stage of infection with *T. b. gambiense*, but is ineffective for *T. b. rhodesiens*. Moreover, pentamidine has side effects such as hypotension and reduction in blood glucose. Melarsoprol, an arsenical agent, exerts an effect in the terminal stage of infection with *T. b. gambiense* and *T. b. rhodesiens* (central neuropathy) due to its penetration of the blood brain barrier. However, it causes encephalopathy because of its strong side effects on the central nervous system. Further, melarsoprol-resistant protozoan strain has emerged.

Eflornithine also penetrates the blood brain barrier and exerts an effect in the terminal stage of infection with melarsoprol-resistant *T. b. gambiense*, for which melarsoprol is ineffective. However, it is ineffective for *T. b. rhodesiens*. Moreover, these drugs has been used for a long time, which brings less effectiveness of said drugs gradually. Similarly, animal trypanosomiasis has been treated with drugs such as diminazene, suramin, isometamidium and a mutagenic substance homidium. Since these drugs have particularly used for a long period, until now protozoa resistant to these drugs have emerged in various regions. Thus posed drastic decrease of the utility of said drugs for treatment of trypanosomiasis become a major problem.

Due to a delay of the development of a new drug, classic existing drugs with strong side effects are still used for the treatment of African sleeping sickness now. Therefore, development of novel and effective drugs for trypanosomiasis in humans and in animals are demanded on a worldwide scale. In addition, as described above, the existing anti human-infectious *trypanosoma* agents are differentially-effective depending on the kind of protozoa and the stage of infection, and are not effective against drug resistant protozoan strains. It is desired to develop an anti-*trypanosoma* agent which is irrespective of the kind of *trypanosoma* protozoa and of the stage of infection, particularly an anti-*trypanosoma* agent which is specifically effective against *T. b. rhodesiens* and in the terminal stage of infection (for central neuropathy), having a novel skeleton with reduced side effects.

In order to solve the aforementioned problems, therapeutic drugs for the treatment of trypanosomiasis have been already reported, but no effective compound has yet been discovered (see Patent Literature 1).

CITATION LIST

Patent Literature

Patent Literature 1: International Publication No. WO 2009/004899

SUMMARY OF INVENTION

Technical Problem

Trypanosomiasis is caused by *trypanosoma* protozoa proliferation in the host cells. Substances that inhibit *trypanosoma* protozoa proliferation are expected to serve as antitrypanosoma drugs that inhibit the development of or alleviate the symptoms of trypanosomiasis. Accordingly, the present invention is objected to provide a novel anti-*trypanosoma* drug which solve the aforementioned problems of the conventional technique.

Solution to Problem

The inventors searched for a substance that inhibits *trypanosoma* protozoa proliferation from metabolites produced by microorganisms, and found a substance with an inhibitory activity on *trypanosoma* protozoa proliferation produced in the culture solution of the actinomycete K10-0216 strain which was newly isolated from soil. Further, the inventors purified and isolated from the above culture product to obtain novel substances having an inhibitory activity on *trypanosoma* protozoa proliferation, those are Mangromicin A and its analogues Mangromicin B and Mangromicin C, thereby achieved the present invention. Substances having the same chemical structures of these Mangromicins were not known previously.

The present invention was achieved based on the aforementioned findings. Specifically, the present invention relates to novel compounds, Mangromicin A, Mangromicin B, and Mangromicin C (hereinbelow, may be collectively referred to as "Mangromicins"). In this specification, Mangromicin A refers to a compound having the following physical properties:

(1) Character: White powder or light yellow powder
(2) Molecular weight: 410
(3) Molecular formula: $C_{22}H_{34}O_7$
(4) $[M+H]^+$ by high resolution mass spectrometry, theoretical value (m/z) 411.2383, actual value (m/z) 411.2377
(5) Specific rotation: $[\alpha]_D^{25.3}=-13.56°$ (c=0.1, methanol)
(6) Ultraviolet absorption maximum (in methanol) $\lambda_{max}$ ($\epsilon$): 251(2747)
(7) Infrared absorption maximum $\epsilon_{max}$ (KBr tablet): Maximum absorption at 3440, 1637 $cm^{-1}$
(8) $^1H$ NMR (in deuterated methanol) δ ppm: 4.73 (1H, d), 2.10 (1H, dd), 2.05 (1H, ddd), 2.88 (1H, ddd), 1.25 (1H, ddd), 2.43 (1H, ddd), 1.62 (1H), 1.85 (1H, dd), 2.55 (1H, m), 3.20 (1H, d, br), 4.30 (1H, d), 3.32 (1H, d), 2.75 (1H, q), 2.50 (1H, d), 4.55 (1H, dd), 1.60 (2H), 1.40 (1H, m), 1.52 (1H, m), 0.95 (3H, t), 1.35 (3H, s), 1.06 (3H, d), 1.03 (3H, d)
(9) $^{13}C$ NMR (in deuterated methanol) δ ppm: 73.8, 44.4, 167.9, 103.4, 19.3, 37.4, 85.0, 48.9, 37.3, 80.2, 73.0, 72.3, 52.7, 223.3, 44.4, 169.3, 34.6, 21.3, 14.4, 24.8, 13.7, 8.5
(10) Solubility: Readily soluble in chloroform, dichloromethane, ethanol, and methanol; and poorly soluble in water.

Alternatively, Mangromicin A described in this specification may also be a compound having the structure represented by the following formula I.

[Chemical formula 1]

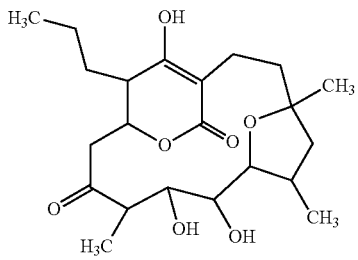

[I]

In this specification, Mangromicin B refers to a compound having the following physical properties:

(1) Character: White powder or light yellow powder
(2) Molecular weight: 392
(3) Molecular formula: $C_{22}H_{32}O_6$
(4) $[M+H]^+$ by high resolution mass spectrometry, theoretical value (m/z) 393.2277, actual value (m/z) 393.2271
(5) Specific rotation: $[\alpha]_D^{25.3}=-24.08°$ (C=0.1, methanol)
(6) Ultraviolet absorption maximum (in methanol) $\lambda_{max}$ ($\epsilon$): 236(8036)
(7) Infrared absorption maximum $\nu_{max}$ (KBr tablet): Maximum absorption at 3450, 1672 $cm^{-1}$
(8) $^1H$ NMR (in deuterated methanol) δ ppm: 4.61 (1H, d), 2.28 (1H, dd), 2.05 (1H, ddd), 2.91 (1H, ddd), 1.27 (1H, m), 2.59 (1H, m), 1.41 (1H, dd), 1.97 (1H, dd), 2.53 (1H, m), 3.68 (1H, dd), 4.54 (1H, dd), 6.74 (1H, d), 2.18 (1H, dd), 4.03 (1H, dd), 1.56 (1H, m), 1.59 (1H, m), 1.36 (1H, m), 1.43 (1H, d), 0.94 (3H, t), 1.37 (3H, s), 1.22 (3H, d)
(9) $^{13}C$ NMR (in deuterated methanol) δ ppm: 78.3, 43.5, 167.4, 104.0, 20.1, 33.8, 82.3, 50.4, 37.3, 84.8, 69.9, 150.7, 134.8, 205.2, 43.3, 168.3, 36.4, 20.7, 14.3, 24.9, 16.5
(10) Solubility: Readily soluble in chloroform, dichloromethane, ethanol, and methanol; and poorly soluble in water.

Alternatively, in this specification, Mangromicin B may also be a compound having the structure represented by the following formula II.

[Chemical formula 2]

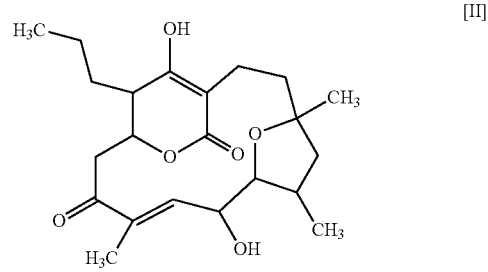 [SMILES: CCCC1C(O)=C2CCC3(C)CC(C)C(O3)C(O)/C=C(\C)C(=O)CC1OC2=O]

[II]

Mangromicin C described in this specification refers to a compound having the following physical properties:

(1) Character: White powder or light yellow powder
(2) Molecular weight: 394
(3) Molecular formula: $C_{22}H_{34}O_6$
(4) $[M+H]^+$ by high resolution mass spectrometry, theoretical value (m/z) 395.2434, actual value (m/z) 395.2413
(5) Specific rotation: $[\alpha]_D^{25.3}=23.24°$ (C=0.1, methanol)
(6) Ultraviolet absorption maximum (in methanol) $\lambda_{max}$ ($\epsilon$): 251(5595)
(7) Infrared absorption maximum $\nu_{max}$ (KBr tablet): Maximum absorption at 3430, 1657 $cm^{-1}$
(8) $^1H$ NMR (in deuterated methanol) δ ppm: 4.78 (1H, d), 2.14 (1H), 2.02 (1H, dd), 2.85 (1H, dddd), 1.25 (1H, ddd), 2.46 (1H), 1.68 (2H, m), 2.74 (1H, m), 1.72 (1H, ddd), 2.43 (1H), 3.56 (1H, ddd), 3.39 (1H), 2.43 (1H), 2.38 (1H), 4.46 (1H), 1.61 (2H, m), 1.38 (1H), 1.52 (1H), 0.96 (3H, t), 1.34 (3H, s), 1.06 (3H, d), 1.04 (3H, d)
(9) $^{13}C$ NMR (in deuterated methanol) δ ppm: 74.0, 43.9, 167.3, 103.7, 19.5, 36.5, 83.7, 49.9, 44.4, 37.6, 69.5, 81.9, 37.0, 212.6, 44.2, 169.2, 35.0, 21.2, 14.4, 25.2, 15.4
(10) Solubility: Readily soluble in chloroform, dichloromethane, ethanol, and methanol; and poorly soluble in water.

Alternatively, in this specification, Mangromicin C may also be a compound having the structure represented by either one of the following formulae IIIa and IIIb.

[Chemical formula 3]

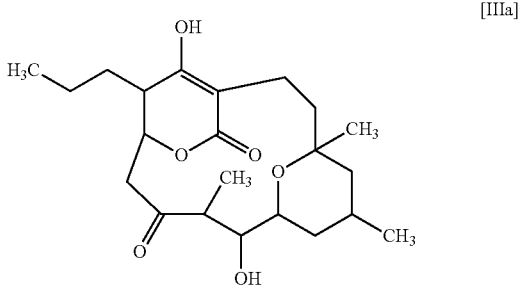

[IIIa]

[Chemical formula 4]

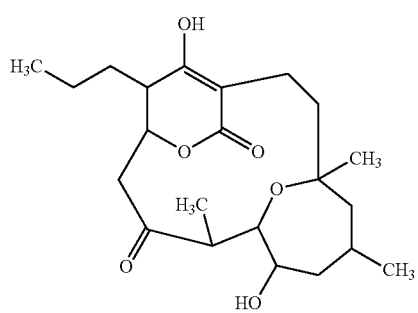

[IIIb]

Since the above-described Mangromicins have hydroxyl groups, their ester compounds are obtainable as prodrugs by using the acylation reaction generally known to those skilled in the art. The invention also encompasses such ester compounds of Mangromicins. Specifically, the present invention encompasses an ester compound in which the hydroxyl group of Mangromicin A, Mangromicin B, or Mangromicin C is linked to a saturated or unsaturated lower fatty acid or higher fatty acid via ester linkage. Examples of acids that give rise to the ester compounds of the Mangromicins of the present invention include aliphatic carboxylic acid such as acetic acid and pentanoic acid; aryl carboxylic acid such as benzoic acid; mono- or di-alkyl carbamic acid; aliphatic sulfonic acid such as propanesulfonic acid; arylsulfonic acid such as benzenesulfonic acid; heterocyclic carboxylic acid such as morpholinyl carboxylic acid, oxazolidinyl carboxylic acid, and azetidine carboxylic acid. Further, the Mangromicins of the present invention also encompass hydrates and solvates of Mangromicins.

The present invention also relates to a method for producing Mangromicins, comprising culturing microorganism which belongs to the Actinomycetales and can produce said Mangromicins in a medium, allowing Mangromicins to accumulate in said culture, and collecting Mangromicins from the culture. In the production method, the microorganisms which belongs to the Actinomycetales and can produce said Mangromicins are preferably the *Lechevalieria* sp. K10-0216 strain (accession number NITE BP-1114).

In an another embodiment, the present invention further relates to a novel actinomycete, the *Lechevalieria* sp. K10-0216 strain. In this specification, the *Lechevalieria* sp. K10-0216 strain refers to the microorganisms that were newly isolated from mangrove soil of Iriomote island, Okinawa, Japan by the inventors, and that were deposited with The National Institute of Technology and Evaluation, International Patent Organism Depositary (2-5-8 Kazusakamatari, Kisarazu-shi, Chiba, Japan), as the *Lechevalieria* sp. K10-0216 strain on Jul. 21, 2011 (accession number NITE BP-1114). The *Lechevalieria* sp. K10-0216 strain of the present invention has the bacteriological properties as described in Example 1 below in this specification.

Further, in an another embodiment, the present invention relates to an agent for inhibiting *trypanosoma* protozoa proliferation and a pharmaceutical composition, comprising the above-described Mangromicin A, Mangromicin B and/or Mangromicin C as an active ingredient. The pharmaceutical composition of the present invention is preferably an anti-*trypanosoma* drug (therapeutic agent and preventive agent for infection with *trypanosoma* protozoa).

Advantageous Effects of the Invention

The Mangromicins of the present invention can inhibit *trypanosoma* protozoa proliferation and thus serve as novel anti-*trypanosoma* drugs. The *Lechevalieria* sp. K10-0216 strain of the present invention can produce Mangromicins and be used for the production of Mangromicins.

DESCRIPTION OF EMBODIMENTS

The Mangromicins of the present invention can be produced by culturing microorganisms which belongs to the Actinomycetales and can produce Mangromicins in a medium, allowing Mangromicins to accumulate in a culture, and collecting (separating, extracting, and purifying) Mangromicins from the culture.

In the production method for the Mangromicins of the present invention, the "microorganisms which belongs to the Actinomycetales and can produce Mangromicins" are not particularly limited as long as they belong to actinomycete and can produce Mangromicins. Bacterial strains to be used for the production method for the Mangromicins of the present invention encompass, in addition to the aforementioned bacterial strain, the mutant strain thereof as well as all of bacteria capable of producing Mangromicins that belong to actinomycete. Whether a candidate microorganism is the "microorganisms which belongs to the Actinomycetales and can produce Mangromicins" can be determined by the following method. Into a 500 mL-triangular flask containing 100 mL of a liquid medium (pH 7.0) composed of 2.4% starch, 0.1% glucose, 0.3% peptone, 0.3% bonito extract, 0.5% yeast extract, and 0.4% calcium bicarbonate, 1 mL of the test microorganisms cultured in a liquid medium are inoculated, followed by shaking culture at 27° C. for three days. Subsequently, 1 mL of the resulting seed culture solution was inoculated into a 500 mL-triangular flask containing 100 mL of a liquid medium (pH 7.0) composed of 2.0% starch, 0.5% glycerol, 1.0% defatted wheat germ, 0.3% bonito meat extract, 0.3% dry yeast, and 0.4% calcium bicarbonate, followed by shaking culture at 27° C. for seven days. When Mangromicins are present in the resulting culture, then that microorganism can be determined as the which belongs to the Actinomycetales and can produce Mangromicins. The microorganism which belongs to the Actinomycetales and can produce Mangromicins is preferably the aforementioned *Lechevalieria* sp. K10-0216 strain.

In this specification, "mutant strain" refers to a strain that possesses different bacteriological properties or genes from the *Lechevalieria* sp. K10-0216 strain through artificial or naturally occurring mutagenic stimulation. Such mutant strains encompass, in addition to bacterial strains derived from the *Lechevalieria* sp. K10-0216 strain, the original bacterial strain from which the *Lechevalieria* sp. K10-0216 strain is derived. In this specification, the mutant strain does not necessarily have to retain traces of actual emergence, and for example, a bacterial strain having genes that are highly homologous (for example, 80% or more, 85% or more, 90% or more, and 95% or more) to the genes of the *Lechevalieria* sp. K10-0216 strain (for example, the 16S rRNA gene (SEQ ID NO: 1)) is also encompassed in the mutant strain. Also, as long as these mutant strains maintain the ability to produce Mangromicins, it does not matter whether they are artificially produced or obtained from nature.

A medium for culturing microorganisms which belongs to the Actinomycetales and can produce Mangromicins can contain, as nutrient sources, substances that can be used as nutrient sources for actinomycete. For example, nitrogen sources such as commercially available peptone, meat extract, corn steep liquor, cottonseed flour, peanut flour, soy flour, yeast extract, NZ-amine, casein hydrates, sodium nitrate, ammonium nitrate and ammonium sulfate; carbohydrates such as glycerol, starch, glucose, galactose and mannose, or carbon sources such as fat; and inorganic salts such as sodium chloride, salts of phosphoric acid, calcium carbonate and magnesium sulfate can be used alone or in combination. In addition, a trace amount of metal salts and, as a defoaming agent, animal, plant and mineral oils and the like can be added to the medium as needed. Said medium additive can be enough as long as it is useful for production of Mangromicins using the producing bacteria, and any of the publicly known culture materials for actinomycete can be used as medium additive.

Cultivation of microorganisms which belongs to the Actinomycetales and can produce Mangromicins can be conducted in a temperature range in which the producing bacteria can grow and produce Mangromicins (for example, 10° C. to 40° C., preferably 25 to 30° C.) for several days to two weeks with shaking. The culture conditions can be appropriately selected according to the properties of Mangromicins producing bacteria to be used by referring the description of this specification.

Mangromicins can be collected by extracting from a culture solution using a water-immiscible organic solvent such as ethyl acetate. In addition to this extraction method, publicly known methods useful for collecting lipid-soluble substances such as adsorption chromatography, partition chromatography, gel filtration chromatography, scrap from thin-layer chromatography, centrifugal countercurrent chromatography, high-performance liquid chromatography and the like can be appropriately combined or repeated to carry out purification until pure Mangromicins are obtained.

The Mangromicins of the present invention can be used as pharmaceutical compositions. Specifically, the Mangromicins of the present invention have inhibiting activity on *trypanosoma* protozoa proliferation and thus can be used as anti-*trypanosoma* drugs (therapeutic drugs or preventive drugs for diseases caused by *trypanosoma* protozoa infection). In this specification, the "*trypanosoma* protozoa" encompasses *T. b. gambiense, T. b. rhodesiens*, and the subgenera of *trypanosoma* protozoa such as *Trypanosoma cruzi, Trypanosoma brucei (T. brucei), Trypanosoma congolense (T. congolense), Trypanosoma vivax (T. vivax), Trypanosoma evansi (T. evansi), Trypanosoma theileri (T. theileri)*, and *Trypanosoma equiperdum (T. equiperdum)*. Diseases caused by *trypanosoma* protozoa infection encompass diseases generally known as trypanosomiasis, for example, nagana, African trypanosomiasis and the like.

The agent for inhibiting *trypanosoma* protozoa proliferation or the pharmaceutical composition of the present invention can be used in the oral dosage form or parenteral dosage form such as in a form for an injection, a drip infusion or the like. When the present compound is administered to mammals, it can be orally administered in the form of a tablet, a powder, a granule, a syrup, and the like, or parenterally administered in the form of an injection or a drip infusion agent. A dosage varies depending on factors such as the severity of symptoms, ages and types of disease, and the agent for inhibiting *trypanosoma* protozoa proliferation or the pharmaceutical composition is normally administered to adults at a dose of 50 mg to 500 mg per one day at once or at several times a day.

The agent for inhibiting *trypanosoma* protozoa proliferation or the pharmaceutical composition of the present invention can be formulated by a conventional method using common pharmaceutically acceptable carriers. In preparing an oral solid preparation, an excipient and, if necessary, a binder, a disintegrant, a lubricant and the like are added to main composition, and then prepared as a solvent, a granule, a powder, a capsule and the like by a conventional method. In preparing an injection, a pH adjuster, a buffer, a stabilizing agent, a solubilizing agent and the like are added to main composition as needed, and then prepared as a subcutaneous or intravenous injection by a conventional method.

EXAMPLES

Hereinbelow, the present invention will be specifically described with reference to Examples, however, the present invention is not limited thereto. It should be noted that all literatures cited throughout the present application are incorporated herein by reference in their entirety. Also, the present application claims priority to Japanese Patent Application No. 2011-191404, the entire content of which is incorporated herein by reference.

Example 1

Bacteriological Properties of the *Lechevalieria* sp. K10-0216 Strain

The *Lechevalieria* sp. K10-0216 strain was newly isolated from mangrove soil in Iriomote island, Okinawa, by the inventors. The bacteriological properties of the *Lechevalieria* sp. K10-0216 strain were as follows.
(I) Morphological Property The vegetative hyphae grow well on various kinds of agar media with no fragmentation observed. The aerial hyphae was barely epiphytic to inorganic salts-starch agar, exhibiting white tone. The aerial hyphae, which are approximately 0.3 to 0.4 μm long, interlace to form an aggregate. Neither sporangium nor zoospore is found.
(II) Characters on Various Kinds of Media Culture characters of the *Lechevalieria* sp. K10-0216 strain examined by the method of E. B. Shirling and D. Gottlieb (International journal of systematic bacteriology, Vol. 16, p. 313 (1966)) are shown in Table 1. Color tone can be determined by referring to The Color Harmony Manual, 4th edition (Container Corporation of America, Chicago, 1958) for the standard color. Color chips are shown along with their codes in parentheses. The results below were observed in each medium after two weeks at 27° C., unless otherwise noted.

TABLE 1

| | | |
|---|---|---|
| sucrose-nitrate agar | growth | medium growth degree, ivory (2db) |
| | rear surface | ivory (2db) |
| | aerial hyphae | not epiphytic |
| | soluble pigment | no production |
| glucose-asparagine agar | growth | low growth degree, light wheat (2ea) |
| | rear surface | fresh pink (3ca) |
| | aerial hyphae | not epiphytic |
| | soluble pigment | no production |
| glycerol-asparagine agar (ISP) | growth | medium growth degree, bamboo (2fb) |
| | rear surface | light wheat (2ea) |
| | aerial hyphae | not epiphytic |
| | soluble pigment | no production |
| inorganic salts-starch agar (ISP) | growth | high growth degree, light ivory (2ca) |
| | rear surface | light ivory (2ca) |
| | aerial hyphae | barely epiphytic, white (a) |
| | soluble pigment | not epiphytic |

TABLE 1-continued

| | | |
|---|---|---|
| tyrosine agar (ISP) | growth | low growth degree, bamboo (2gc) |
| | rear surface | bisque (3ec) |
| | aerial hyphae | not epiphytic |
| | soluble pigment | no production |
| oatmeal agar (ISP) | growth | high growth degree, light ivory (2ca) |
| | rear surface | fresh pink (3ca) |
| | aerial hyphae | not epiphytic |
| | soluble pigment | no production |
| yeast-malt extract agar (ISP) | growth | high growth degree, bamboo (2fb) |
| | rear surface | light wheat (2ca) |
| | aerial hyphae | not epiphytic |
| | soluble pigment | no production |
| nutrient agar | growth | high growth degree, bamboo (2fb) |
| | rear surface | bamboo (2fb) |
| | aerial hyphae | not epiphytic |
| | soluble pigment | no production |
| peptone-yeast-iron agar (ISP) | growth | high growth degree, bisque (3ec) |
| | rear surface | bamboo (2gc) |
| | aerial hyphae | not epiphytic |
| | soluble pigment | no production |
| glucose-nitrate agar | growth | low growth degree, ivory (2db) |
| | rear surface | ivory (2db) |
| | aerial hyphae | not epiphytic |
| | soluble pigment | no production |
| glycerol-calcium malate agar | growth | medium growth degree, light ivory (2ca) |
| | rear surface | ivory (2db) |
| | aerial hyphae | not epiphytic |
| | soluble pigment | no production |
| glucose -peptone agar | growth | medium growth degree, light wheat (2ea) |
| | rear surface | light wheat (2ea) |
| | aerial hyphae | not epiphytic |
| | soluble pigment | no production |

(III) Physiological Properties
(1) Melanin pigment production
  (a) Tyrosine agar: Negative
  (b) Peptone-Yeast-Iron agar: Negative
  (c) Trypton-Yeast extract: Negative
(2) Gelatin liquefaction (simple gelatin medium) (20° C.) Negative
(3) Starch hydrolysis: Positive
(4) Skim milk solidification (37° C.): Positive
(5) Skim milk peptonization (37° C.): Positive
(6) Growth temperature range: 12 to 40° C.
(7) Carbon source utilization (Pridham-Gottlieb agar medium)
Utilized: D-glucose, L-arabinose, D-xylose, melibiose, D-mannitol, D-fructose, myo-inositol and sucrose
Slightly utilized: raffinose and L-rhamnose
(8) Cellulose degradation: Negative
(IV) Cellular Chemical Composition
Diaminopimelic acid in the cell wall is the meso form. The major menaquinone is MK-9($H_4$), and MK-8($H_4$) and MK-10 ($H_4$) are contained in small amounts.
(V) 16S rRNA Gene Analysis
In the 16S rRNA gene, approximately 1400 bases were sequenced (SEQ ID NO: 1). From the results of system analysis by the neighbor-joining method using the data of bacterial strains belonging to the genus *Lechevalieria* and other actinomycetes registered and published in DNA database, it is reasonable to classify the subject bacterial strain into the genus *Lechevalieria*, and the bacterial strain is most closely related to *Lechevalieria* aerocolonigenes.

(VI) Conclusion
The bacteriological properties of the subject bacteria specified above are summarized as follows. Diaminopimelic acid in the cell wall is the meso form and the major menaquinone is MK-9($H_4$). The aerial hyphae is slightly epiphytic and interlace to form an aggregate. Colonies exhibit light yellow color and do not produce melanin pigment. From the above results and the analytical results of the 16S rRNA gene, the subject bacterial strain was determined to be one bacterial species belonging to the genus *Lechevalieria*, which was published in International Journal of Systematic and Evolutionary Microbiology in 2001. The subject bacterial strain was deposited at The Patent Microorganisms Depositary, National Institute of Technology and Evaluation (2-5-8 Kazusakamatari, Kisarazu-shi, Chiba), as *Lechevalieria* sp. K10-0216 on Jul. 21, 2011 (accession number NITE BP-1114).

Example 2

Preparation of Mangromicins A, B, and C 1 mL of *Lechevalieria* sp. K10-0216 (accession number NITE BP-1114) cultured in a liquid medium was inoculated into each of 60 of 500-mL triangular flasks each containing 100 mL of a liquid medium (pH 7.0) composed of 2.4% starch, 0.1% glucose, 0.3% peptone (Kyokuto Pharmaceutical Industrial Co., Ltd.), 0.3% bonito extract (Kyokuto Pharmaceutical Industrial Co., Ltd.), 0.5% yeast extract (Oriental Yeast Co., Ltd.), and 0.4% calcium bicarbonate, followed by incubating the culture with shaking at 27° C. for three days. Then, 1 mL of the resulting seed culture solution was inoculated each of 60 of 500-mL triangular flasks each containing 100 mL of a liquid medium (pH 7.0) composed of 2.0% starch, 0.5% glycerol, 1.0% defatted wheat germ (Nisshin Pharma Inc.), 0.3% bonito meat extract (Kyokuto Pharmaceutical Industrial Co., Ltd.), 0.3% dry yeast (JT Foods, Co., Ltd.), and 0.4% calcium bicarbonate, followed by incubation of culture with shaking at 27° C. for seven days.

After completion of culture, 100 mL of ethanol was added to each of the 60 of 500-mL triangular flasks, followed by vigorous stirring for one hour. Subsequently, ethanol in the resulting extract was distilled under reduced pressure, and 3 L of ethyl acetate was added to the obtained aqueous solution, which were thoroughly stirred. The resulting ethyl acetate layer was collected and concentrated to dryness using an evaporator, whereby 5.36 g of a crude purified product 1 was obtained. Subsequently, in order to remove lipid, liquid-liquid partition was performed using hexane/methanol to collect resulting methanol layer, from which methanol was distilled by an evaporator, whereby 4.26 g of a crude purified product 2 was obtained. This product was dissolved in a small amount of methanol and subjected to open column chromatography with silica gel (Merck & Co., Inc.) with the chloroform-methanol solvent system for stepwise elution (100:0, 100:1, 50:1, 10:1, 1:1, 0:100), whereby a 10:1 fraction containing Mangromicins A and C (crude purified product 3), a 50:1 fraction containing Mangromicins A, B, and C (crude purified product 4), and a 100:1 fraction containing Mangromicins B and C (crude purified product 5) were obtained in amounts of 307.4 mg, 221.8 mg, and 251.9 mg, respectively.

The crude purified product 3 and/or crude purified product 4 was dissolved in a small amount of methanol and subjected to open column chromatography with ODS (Fuji Silysia Chemical, Ltd.) with the methanol-aqueous solvent system for stepwise elution (20:80, 40:60, 50:50, 60:40, 80:20, 100:0), whereby a 60:40 fraction containing Mangromicin A (crude purified product 6) was obtained. The crude purified product 6 was dissolved in methanol and injected in an octadecylsilyl column (Inertsil ODS-4, a diameter of 10×250 mm, a flow rate of 4.5 mL/min, detection at 254 nm), which was subjected to high-performance liquid chromatography and eluted with methanol-water (50:50). The peak near a retention time of 25 minutes was obtained as a fraction and concentrated under reduced pressure, whereby 9 mg of Mangromicin A was obtained as white powder or light yellow powder.

The crude purified product 4 and/or crude purified product 5 was dissolved in a small amount of methanol and subjected to open column chromatography with ODS (Fuji Silysia Chemical, Ltd.) with the methanol-aqueous solvent system for stepwise elution (20:80, 40:60, 50:50, 60:40, 80:20, 100:0), whereby a 60:40 fraction containing Mangromicin B (crude purified product 7) was obtained. The crude purified product 7 was dissolved in methanol and injected in an octadecylsilyl column (Inertsil ODS-4, a diameter of 10×250 mm, a flow rate of 4.5 mL/min, detection at 254 nm), which was subjected to high-performance liquid chromatography and eluted with methanol-water (60:40). The peak near a retention time of 20 minutes was obtained as a fraction and concentrated under reduced pressure, whereby 10.3 mg of Mangromicin B was obtained as white powder or light yellow powder.

The crude purified product 3 and/or crude purified product 4 and/or crude purified product 5 was dissolved in a small amount of methanol and subjected to open column chromatography with ODS (Fuji Silysia Chemical, Ltd.) with the methanol-aqueous solvent system for stepwise elution (20:80, 40:60, 50:50, 60:40, 80:20, 100:0), whereby a 60:40 fraction containing Mangromicin C (crude purified product 8) was obtained. The crude purified product 8 was dissolved in methanol and injected in an octadecylsilyl column (Inertsil ODS-4, a diameter of 10×250 mm, a flow rate of 4.5 mL/min, detection at 254 nm), which was subjected to high-performance liquid chromatography and eluted with methanol-water (60:40). The peak near a retention time of 15 minutes was obtained as a fraction and concentrated under reduced pressure, whereby 21.7 mg of Mangromicin C was obtained as white powder or light yellow powder.

The results of measuring the physicochemical properties of thus obtained Mangromicin A, Mangromicin B and Mangromicin C were as follows.

Mangromicin A
(1) Character: White powder or light yellow powder
(2) Molecular weight: 410
(3) Molecular formula: $C_{22}H_{34}O_7$
$[M+H]^+$ by high resolution mass spectrometry, theoretical value (m/z) 411.2383, actual value (m/z) 411.2377
(4) Specific rotation: $[\alpha]_D^{25.3} = -13.56°$ (c=0.1, methanol)
(5) Ultraviolet absorption maximum $\lambda_{max}$ (in methanol): 251 (2747) (the number in parenthesis indicates $\epsilon$)
(6) Infrared absorption maximum $\nu_{max}$ (KBr tablet): Maximum absorption at 3440, 1637 $cm^{-1}$
(7) Proton nuclear magnetic resonance spectrum: Chemical shifts (ppm) in deuterated methanol are shown in Table 2 (in the Table, s represents a singlet, d a doublet, m a multiplet, and H the number of protons).
(8) Carbon nuclear magnetic resonance spectrum: Chemical shifts (ppm) in deuterated methanol are shown in Table 2.
(9) Solubility in solvents: Readily soluble in chloroform, dichloromethane, ethanol, and methanol. Poorly soluble in water.

TABLE 2

| No. | $\delta_C$ | $\delta_H$ | M | Int |
|---|---|---|---|---|
| 1 | 73.8 | 4.73 | d | 1H |
| 2 | 44.4 | 2.10 | dd | 1H |
| 3 | 167.9 | | | |
| 4 | 103.4 | | | |
| 5 | 19.3 | 2.05 | ddd | 1H |
| | | 2.88 | ddd | 1H |
| 6 | 37.4 | 1.25 | ddd | 1H |
| | | 2.43 | ddd | 1H |
| 7 | 85.0 | | | |
| 8 | 48.9 | 1.62 | — | 1H |
| | | 1.85 | dd | 1H |
| 9 | 37.3 | 2.55 | m | 1H |
| 10 | 80.2 | 3.20 | d, br | 1H |
| 11 | 73.0 | 4.30 | d | 1H |
| 12 | 72.3 | 3.32 | d | 1H |
| 13 | 52.7 | 2.75 | q | 1H |
| 14 | 223.3 | | | |
| 15 | 44.4 | 2.50 | d | 1H |
| | | 4.55 | dd | 1H |
| 16 | 169.3 | | | |
| 1' | 34.6 | 1.60 | — | 2H |
| 2' | 21.3 | 1.40 | m | 1H |
| | | 1.52 | m | 1H |
| 3' | 14.4 | 0.95 | t | 3H |
| 7-Me | 24.8 | 1.35 | s | 3H |
| 9-Me | 13.7 | 1.06 | d | 3H |
| 13-Me | 8.5 | 1.03 | d | 3H |

Mangromicin B
(1) Character: White powder or light yellow powder
(2) Molecular weight: 392
(3) Molecular formula: $C_{22}H_{32}O_6$
$[M+H]^+$ by high resolution mass spectrometry, theoretical value (m/z) 393.2277, actual value (m/z) 393.2271
(4) Specific rotation: $[\alpha]_D^{25.3} = -24.08°$ (C=0.1, methanol)
(5) Ultraviolet absorption maximum $\lambda_{max}$ (in methanol): 236(8036) (the number in parenthesis indicates $\epsilon$)
(6) Infrared absorption maximum $\nu_{max}$ (KBr tablet): Maximum absorption at 3450, 1672 $cm^{-1}$
(7) Proton nuclear magnetic resonance spectrum: Chemical shifts (ppm) in deuterated methanol are shown in Table 3 (in the Table, s represents a singlet, d a doublet, m a multiplet, and H the number of protons).
(8) Carbon nuclear magnetic resonance spectrum: Chemical shifts (ppm) in deuterated methanol are shown in Table 3.
(9) Solubility in solvents: Readily soluble in chloroform, dichloromethane, ethanol, and methanol. Poorly soluble in water.

TABLE 3

| No. | δC | δH | M | Int |
|---|---|---|---|---|
| 1 | 78.3 | 4.61 | d | 1H |
| 2 | 43.5 | 2.28 | dd | 1H |
| 3 | 167.4 | | | |
| 4 | 104.0 | | | |
| 5 | 20.1 | 2.05 | ddd | 1H |
| | | 2.91 | ddd | 1H |
| 6 | 33.8 | 1.27 | m | 1H |
| | | 2.59 | m | 1H |
| 7 | 82.3 | | | |
| 8 | 50.4 | 1.41 | dd | 1H |
| | | 1.97 | dd | 1H |
| 9 | 37.3 | 2.53 | m | 1H |
| 10 | 84.8 | 3.68 | dd | 1H |
| 11 | 69.9 | 4.54 | dd | 1H |
| 12 | 150.7 | 6.74 | d | 1H |
| 13 | 134.8 | | | |
| 14 | 205.2 | | | |

TABLE 3-continued

| No. | δC | δH | M | Int |
|---|---|---|---|---|
| 15 | 43.3 | 2.18 | dd | 1H |
|  |  | 4.03 | dd | 1H |
| 16 | 168.3 |  |  |  |
| 1' | 36.4 | 1.56 | m | 1H |
|  |  | 1.59 | m | 1H |
| 2' | 20.7 | 1.36 | m | 1H |
|  |  | 1.43 | d | 1H |
| 3' | 14.3 | 0.94 | t | 3H |
| 7-Me | 24.9 | 1.37 | s | 3H |
| 9-Me | 16.5 | 1.22 | d | 3H |

Mangromicin C (1) Character: White powder or light yellow powder (2) Molecular weight: 394

(3) Molecular formula: $C_{22}H_{34}O_6$ $[M+H]^+$ by high resolution mass spectrometry, theoretical value (m/z) 395.2434, actual value (m/z) 395.2413

(4) Specific rotation: $[\alpha]_D^{25.3} = 23.24°$ (C=0.1, methanol)

(5) Ultraviolet absorption maximum (in methanol): 251 (5595) (the number in parenthesis indicates $\epsilon$)

(6) Infrared absorption maximum $\nu_{max}$ (KBr tablet): Maximum absorption at 3430, 1657 $cm^{-1}$ (7) Proton nuclear magnetic resonance spectrum: Chemical shifts (ppm) in deuterated methanol are shown in Table 4 (in the Table, s represents a singlet, d a doublet, m a multiplet, and H the number of protons).

(8) Carbon nuclear magnetic resonance spectrum: Chemical shifts (ppm) in deuterated methanol are shown in Table 4.

(9) Solubility in solvents: Readily soluble in chloroform, dichloromethane, ethanol, and methanol. Poorly soluble in water.

TABLE 4

| No. | δC | δH | M | Int |
|---|---|---|---|---|
| 1 | 74.0 | 4.78 | d | 1H |
| 2 | 43.9 | 2.14 |  | 1H |
| 3 | 167.3 |  |  |  |
| 4 | 103.7 |  |  |  |
| 5 | 19.5 | 2.02 | dd | 1H |
|  |  | 2.85 | dddd | 1H |
| 6 | 36.5 | 1.25 | ddd | 1H |
|  |  | 2.46 |  | 1H |
| 7 | 83.7 |  |  |  |
| 8 | 49.9 | 1.68 | m | 2H |
| 9 | 44.4 | 2.74 | m | 1H |
| 10 | 37.6 | 1.72 | ddd | 1H |
|  |  | 2.43 |  | 1H |
| 11 | 69.5 | 3.56 | ddd | 1H |
| 12 | 81.9 | 3.39 |  | 1H |
| 13 | 37.0 | 2.43 |  | 1H |
| 14 | 212.6 |  |  |  |
| 15 | 44.2 | 2.38 |  | 1H |
|  |  | 4.46 |  | 1H |
| 16 | 169.2 |  |  |  |
| 1' | 35.0 | 1.61 | m | 2H |
| 2' | 21.2 | 1.38 |  | 1H |
|  |  | 1.52 |  | 1H |
| 3' | 14.4 | 0.96 | t | 3H |
| 7-Me | 25.2 | 1.34 | s | 3H |
| 9-Me | 15.4 | 1.06 | d | 3H |
| 13-Me | — | 1.04 | d | 3H |

As a result of studying various physicochemical properties and spectral data of Mangromicin A, it was determined that Mangromicin A had a structure represented by the following formula I.

[Chemical formula 5]

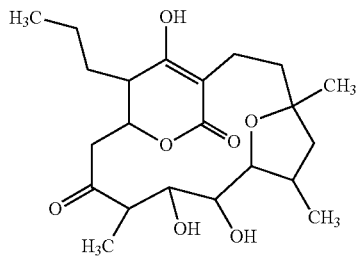

[I]

Also, as a result of studying various physicochemical properties and spectral data of Mangromicin B, it was determined that Mangromicin B had a structure represented by the following formula II.

[Chemical formula 6]

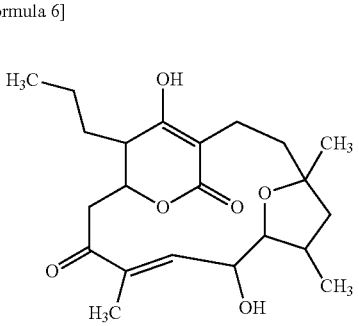

[II]

Also, as a result of studying various physicochemical properties and spectral data of Mangromicin C, it was determined that Mangromicin C had a structure represented by either one of the following formulae IIIa and IIIb.

[Chemical formula 7]

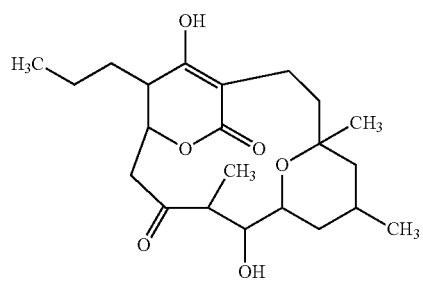

[IIIa]

[Chemical formula 8]

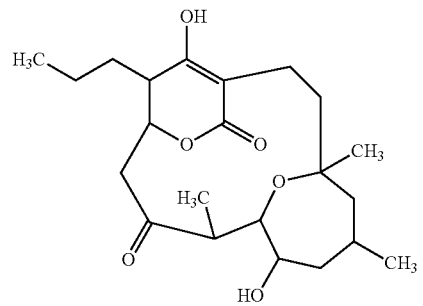

[IIIb]

There has been no report on compounds that coincide with Mangromicins A, B, and C for which various physicochemical properties were obtained as above previously. Hence, it is assumed that Mangromicins A, B, and C are novel substances.

Example 3

Inhibitory Activity on *Trypanosoma* Protozoa Proliferation

The in vitro activities of Mangromicin A, B and C of the present invention to inhibit *trypanosoma* protozoa proliferation were examined as follows.

As the test protozoa, the *Trypanosoma brucei brucei* GUTat 3.1 strain (can be provided by Mr. Yoshisada Yabu, an instructor at Nagoya City University, Graduate School of Medical Sciences, Medical School), which is the causative *trypanosoma* protozoa of nagana, was used. Maintenance and subculture of *trypanosoma* protozoa was carried out by a method which was slightly modified the method of Yabu, et al. [Yabu Y, Koide T, Ohota N, Nose M, and Ogihara Y. Continuous growth of bloodstream forms of *Trypanosoma brucei brucei* in axenic culture system containing a low concentration of serum. Southeast Asian J. Trop. Med. Public Health, 29: 591 to 595 (1998)]. That is, in each well of a 24 well plate, *trypanosoma* protozoa were continuously cultured in the Iscove's Modified Dulbecco's Medium (IMDM) containing 10% inactivated fetal bovine serum (FBS), antibiotics, and various supplements at 37° C. in 5% $CO_2$-95% air by exchanging the medium every one to three days.

The in vitro anti-*trypanosoma* activities of these compounds were measured in accordance with the method of Otoguro et al. [Otoguro K, Ishiyama A, Namatame M, Nishihara A, Furusawa T, Masuma R, Takahashi Y, Shiomi K, Yamada H, and Omura S. Selective and Potent in vitro anti-*trypanosoma* activities of ten microbial metabolites. J. Antibiotics, 61: 372 to 378 (2008)]. That is, to each well of a 96 well plate, 95 µL of a suspension of precultured protozoa (adjusted to a protozoan count of 2.0 to $2.5 \times 10^4$/mL) and 5 µL of a compound solution (50% aqueous solution of ethanol) were added, which were mixed and then incubated at 37° C. in 5% $CO_2$-95% air for 72 hours.

After incubation, the proliferation of protozoa was measured as follows: to each well of the 96 well plate, 10 µL of the Alamar Blue reagent (Sigma-Aldorich, USA) was added, which was then mixed and incubated at 37° C. in 5% $CO_2$-95% air for three to six hours. The presence or absence of protozoan proliferation was determined by colorimetric quantification by measuring the redox potential of the protozoa by measuring the fluorescent intensity using a fluorescence microplate reader (BioTek Instruments, Inc., USA) at an excitation wavelength of 528/20 nm and a fluorescent wavelength of 590/35 nm. The 50% inhibiting concentrations ($IC_{50}$ values) of protozoan proliferation for the present compounds were calculated from the compound concentration action curve created by KC-4 software (Bio-Tek Instruments, Inc., USA) attached to the fluorescence microplate reader.

For comparison, suramin and eflornithine (provided by Prof. R. Brun, Swiss Tropical Institute, Basel, Switzerland) were used as known anti-*trypanosoma* agents, whose effects on cultured *trypanosoma* protozoa had been measured.

The anti-*trypanosoma* activities of the present compounds and known anti-*trypanosoma* agents on cultured *trypanosoma* protozoa were as shown in Table 5 below.

TABLE 5

| Compound | IC50 value (µg/ml) *Trypanosoma brucei brucei* GUTat3.1 strain |
|---|---|
| Mangromicin A | 2.44 |
| Mangromicin B | 43.39 |
| Mangromicin C | 8.90 |
| Suramin | 1.58 |
| Eflornithine | 2.27 |

The anti-*trypanosoma* activities ($IC_{50}$ values) of Mangromicins A, B and C of the present invention on the T.b.b. GUTat 3.1 strain were 2.44, 43.39, and 8.90 µg/mL, respectively, showing that, among these Mangromicins, Mangromicin A had the best anti-*trypanosoma* activity. Compared to existing anti-*trypanosoma* agents, the anti-*trypanosoma* activity of Mangromicin A was equivalent or slightly inferior to suramin and eflornithine. The anti-*trypanosoma* activities of Mangromicins B and C were 1/19 to 1/28 times and 1/4 to 1/6 times of that of suramin and eflornithine, respectively.

Example 4

Cytotoxicity Test

The cytotoxicity test of Mangromicins A, B and C of the present invention was carried out in accordance with the method of Otoguro et al. [Otoguro K, Kohana A, Manabe C, Ishiyama A, Ui H, Shiomi K, Yamada H, and Omura S. Potent antimalarial activities of polyether antibiotic, X-206. J. Antibiotics, 54: 658 to 663, (2001)]. That is, the human fetal lung-derived normal fibroblast MRC-5 cells [can be provided by Dr. L. Maes (Tibotec NV, Mechelen, Belgium)] were maintained and subcultured in the MEM-medium containing 10% bovine fetal serum (FCS) and antibiotics and were used as the host cell model.

A suspension of the human fetal lung-derived normal fibroblast MRC-5 cells was adjusted to $1 \times 10^3$ cells/mL with 10% FCS-MEM, and 100 µL of the resulting suspension was added to a 96 well plate, which was mixed and incubated at 37° C. in 5% $CO_2$-95% air for 24 hours. Subsequently, 90 µL of 10% FCS-MEM and 10 µL of a solution of each of the present compounds (50% aqueous solution of ethanol) were added to each well of the 96 well plate, which was mixed and cultured at 37° C. in 5% $CO_2$-95% air for seven days. The presence or absence of the proliferation of the MRC-5 cells was measured by colorimetric quantification by the MTT assay. The 50% inhibitory concentrations ($IC_{50}$ values) of cell proliferation for the present compounds were calculated from the compound concentration action curve. Also, the selectivity index (SI) was calculated as ($IC_{50}$ values for cytotoxicity)/($IC_{50}$ values for anti-*trypanosoma* activity).

The results of calculation pertaining to $IC_{50}$ and selectivity index are shown in Table 6 below.

TABLE 6

| Compound | IC50 value (µg/ml) MRC-5 cell | Selectivity Index (SI) Try/MRC-5 |
|---|---|---|
| Mangromicin A | 16.02 | 6.6 |
| Mangromicin B | 92.60 | 2.1 |
| Mangromicin C | >100 | >11.2 |
| Suramin | >100 | >63 |
| Eflornithine | >100 | >44 |

The cytotoxicities ($IC_{50}$ values) of Mangromicins A, B and C of the present invention on the human fetal lung-derived normal fibroblast MRC-5 cells were 16.02, 92.60 and >100 µg/mL, respectively, and the selectivity indexes (SI) of Mangromicins A, B and C of the present invention for the anti-*trypanosoma* activity were 6.6, 2.1 and >11.2, respectively. In comparison to existing anti-*trypanosoma* agents, SI of Mangromicin A indicated selective toxicity with >1/9.5 times of pentamidine and with >1/6.7 times of suramin.

Example 5

Antibacterial Activity

The antibacterial activities of Mangromicins A, B and C of the present invention were measured by the following method. Filter paper discs (Advantec, a diameter of 6 mm) were impregnated with 10 μL of 1 mg/mL solutions of Mangromicins A, B and C in methanol, and air-dried for a certain period of time to remove the solvent. Subsequently, the discs were placed on agar plates each containing the test bacteria shown in Table 7, followed by culturing at 35° C. for 24 hours. The diameter of the growth inhibiting zones formed around the paper discs was measured.

The results of the diameter of inhibiting zones measured as the anti-bacterial activities of Mangromicins A, B and C on the test bacteria are shown in Table 7.

TABLE 7

| Test Bacteria | the diameter of inhibiton zones (mm) Mangromicin | | |
|---|---|---|---|
| | A | B | C |
| *Staphylococcus aureus* ATCC6538p | — | — | — |
| *Bacillus subtilis* ATCC6633 | — | 7 | — |

TABLE 7-continued

| Test Bacteria | the diameter of inhibiton zones (mm) Mangromicin | | |
|---|---|---|---|
| | A | B | C |
| *Micrococcus luteus* ATCC9341 | — | — | — |
| *Mycobacterium smegmatis* ATCC607 | — | — | — |
| *Escherichia coli* NIHJ | — | — | — |
| *Escherichia coli* NIHJ JC-2 (IF012734) | — | — | — |
| *Pseudomonas aeruginosa* IF03080 | — | — | — |
| *Xanthomonas campestris* pv. *oryzae* KB88 | — | — | — |
| *Bacteroides fragilis* ATCC 23745 | — | — | — |
| *Acholeplasma laidrawii* KB174 | — | — | — |
| *Candida albicans* KF1 | — | — | — |
| *Saccharomyces cerevisiae* KF26 | — | — | — |
| *Pyricularia oryzae* KF180 | — | — | — |
| *Aspergillus niger* ATCC6275 | — | — | — |
| *Mucor racemosus* IF04581 | — | — | — |

Mangromicins A, B and C of the present invention showed almost no antibacterial activities on the microorganisms listed in Table 7. Thus, it can be presumed that Mangromicins A, B and C of the present invention are specific for *trypanosoma* protozoa.

From the above results, Mangromicins A, B and C of the present invention have inhibitory effects on proliferation of *trypanosoma* protozoa, are less cytotoxic, and exhibit no inhibitory actions on the proliferation of other microorganisms, which suggests that Mangromicins A, B and C are extremely potent as drugs such as an agent for inhibiting *trypanosoma* protozoa or anti-*trypanosoma* agents.

The invention claimed is:

1. A compound represented by the following formula I

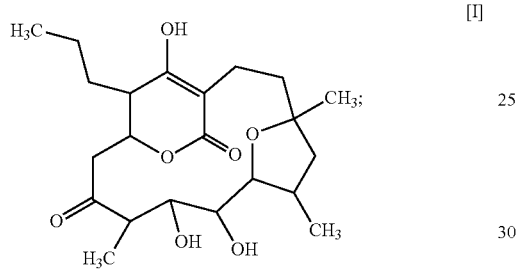

[I]

wherein the compound has a molecular weight of 410, a molecular formula of $C_{22}H_{34}O_7$, an infrared absorption maximum at 3440 and 1637 cm$^{-1}$, $^1$H NMR data in deuterated methanol of δ ppm:

4.73 (1H, d), 2.10 (1H, dd), 2.05 (1H, ddd), 2.88 (1H, ddd), 1.25 (1H, ddd), 2.43 (1H, ddd), 1.62 (1H), 1.85 (1H, dd), 2.55 (1H, m), 3.20 (1H, d, br), 4.30 (1H, d), 3.32 (1H, d), 2.75 (1H, q), 2.50 (1H, d), 4.55 (1H, dd), 1.60 (2H), 1.40 (1H, m), 1.52 (1H, m), 0.95 (3H, t), 1.35 (3H, s), 1.06 (3H, d), 1.03 (3H, d), and $^{13}$C NMR data in deuterated methanol of δ ppm:
73.8, 44.4, 167.9, 103.4, 19.3, 37.4, 85.0, 48.9, 37.3, 80.2, 73.0, 72.3, 52.7, 223.3, 44.4, 169.3, 34.6, 21.3, 14.4, 24.8, 13.7, 8.5.

2. A compound represented by the following formula II

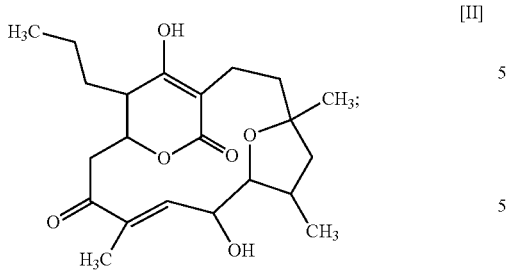

[II]

wherein the compound has a molecular weight of 392, a molecular formula of $C_{22}H_{32}O_6$, an infrared absorption maximum at 3450 and 1672 cm$^{-1}$, $^1$H NMR data in deuterated methanol of δ ppm:

4.61 (1H, d), 2.28 (1H, dd), 2.05 (1H, ddd), 2.91 (1H, ddd), 1.27 (1H, m), 2.59 (1H, m), 1.41 (1H, dd), 1.97 (1H, dd), 2.53 (1H, m), 3.68 (1H, dd), 4.54 (1H, dd), 6.74 (1H, d), 2.18 (1H, dd), 4.03 (1H, dd), 1.56 (1H, m), 1.59 (1H, m), 1.36 (1H, m), 1.43 (1H, d), 0.94 (3H, t), 1.37 (3H, s), 1.22 (3H, d), and $^{13}$C NMR data in deuterated methanol of δ ppm:
78.3, 43.5, 167.4, 104.0, 20.1, 33.8, 82.3, 50.4, 37.3, 84.8, 69.9, 150.7, 134.8, 205.2, 43.3, 168.3, 36.4, 20.7, 14.3, 24.9, 16.5.

3. A production method for the compound of claim 1 which comprises, culturing microorganisms which belongs to Actinomycetales and can produce said compound in a culture medium, allowing the compound to accumulate in the culture medium, and collecting the compound from the culture medium, wherein the microorganism which belongs to Actinomycetales is *Lechevalieria* sp. K10-0216 (accession number NITE BP-1114).

4. An agent having an activity to inhibit proliferation of *trypanosoma* protozoa, comprising the compound of claim 1 as an active ingredient.

5. An anti-*trypanosoma* agent, comprising the compound of claim 1 as an active ingredient.

* * * * *

SEQUENCE LISTING

<160> NUMBER OF SEQ ID NOS: 1

<210> SEQ ID NO 1
<211> LENGTH: 1393
<212> TYPE: DNA
<213> ORGANISM: Lechevalieria sp.

<400> SEQUENCE: 1

```
atcatggctc aggacgaacg ctggcggcgt gcttaacaca tgcaagtcga gcggtaggcc      60
cttcggggta cacgagcggc gaacgggtga gtaacacgtg ggtaacctgc cctgtactct     120
gggataagcc ttggaaacga ggtctaatac cggatacgac cyttgaaggc atsttckkgg     180
gtggaaagtt ccggcggtat gggatggacc cgcggcctat cagcttgttg gtggggtaat     240
ggcctaccaa ggcgacgacg ggtagccggc ctgagagggt gaccggccac actgggactg     300
agacacggcc cagactccta cgggaggcag cagtgggaa tattgcacaa tgggcgaaag     360
cctgatgcag cgacgccgcg tgagggatga cggccttcgg gttgtaaacc tctttcagca     420
gggacgaagc gcaagtgacg gtacctgcag aagaagcacc ggctaactac gtgccagcag     480
ccgcggtaat acgtagggtg cgagcgttgt ccggaattat gggcgtaaa gagctcgtag      540 gcggtttgtc gcgtcggccg tgaaaacttg gggcttaacc ccgagcctgc ggtcgatacg     600
ggcagacttg agttcggcag gggagactgg aattcctggt gtagcggtga aatgcgcaga     660
tatcaggagg aacaccggtg gcgaaggcgg gtctctgggc cgatactgac gctgaggagc     720
gaaagcgtgg ggagcgaaca ggattagata ccctggtagt ccacgccgta aacggtgggt     780
gctaggtgtg gggacttcc acgttctccg tgccgcagct aacgcattaa gcaccccgcc      840
tggggagtac ggccgcaagg ctaaaactca aaggaattga cgggggcccg cacaagcggc     900
```

```
ggagcatgtg gattaattcg atgcaacgcg aagaaccttg cctgggcttg acatgcactg    960
gaaaccggta gagatatcgg cccccttgtg gccggtgtac aggtggtgca tggctgtcgt   1020
cagctcgtgt cgtgagatgt tgggttaagt cccgcaacga gcgcaaccct cgttccatgt   1080
tgccagcgcg ttatggcggg gactcatggg agactgccgg ggtcaactcg gaggaaggtg   1140
gggatgacgt caagtcatca tgcccttat gtccagggct tcacacatgc tacaatggcc    1200
ggtacaaagg gctgcgaagc cgtgaggtgg agcgaatccc ataaagccgg tctcagttcg   1260
gatcggggtc tgcaactcga ccccgtgaag tcggagtcgc tagtaatcgc agatcagcaa   1320
cgctgcggtg aatacgttcc cgggccttgt acacaccgcc cgtcacgtca cgaaagtcgg   1380
taacacctga agc                                                     1393
```